US00PP08221P

United States Patent [19]

Bak et al.

[11] Patent Number: Plant 8,221

[45] Date of Patent: May 4, 1993

[54] GUZMANIA PLANT NAMED ULTRA

[75] Inventors: Gerardus J. Bak, AA Assendelft; Nicolaas D. Steur, JL Oude Niedorp; Elly Bak, ER Rijsenhout, all of Netherlands

[73] Assignee: Corn. Bak B.V., Assendelft, Netherlands

[21] Appl. No.: 765,005

[22] Filed: Sep. 24, 1991

[51] Int. Cl.[5] ..... A01H 5/00

[52] U.S. Cl. ..... Plt./88.8

[58] Field of Search ..... Plt./88.1, 88.6, 88.8

*Primary Examiner*—James R. Feyrer
*Assistant Examiner*—Erich Veitenheimer
*Attorney, Agent, or Firm*—Foley & Lardner

[57] ABSTRACT

A new cultivar of Guzmania named Ultra, characterized by its purple, star shaped inflorescence, superior floral bract production, strong, compact growth habit, and its relatively small size.

2 Drawing Sheets

The present invention relates to a new and distinct cultivar of *Guzmania lingulata*, hereinafter referred to by the cultivar name Ultra. Guzmania comprise a genus within the family bromeliaceae. The new cultivar is a hybrid resulting from a cross of unnamed parent plants identified below.

Guzmania comprise a genus of over 100 species of evergreen perennials suitable for cultivation in the home or under glass. Guzmania are predominantly epiphytic with a few terrestrial species and are native to the tropics. For the most part the species vary in diameter from 7 or 8 inches to 3 or 4 feet and have rosettes of glossy, smooth edged leaves.

Floral bracts of Guzmania frequently have brilliant colors and may last for many months. The range of flower colors for Guzmania varies considerably but is generally in the orange, red and red-purple ranges. White or yellow, tubular, three petalled flowers may also appear on a stem or within the leaf rosette but are usually short lived.

Guzmania may be advantageously grown as pot plants for greenhouse or home use. Desirably the plants are shaded from direct sunlight and during the spring to autumn period, the central vase-like part of the leaf rosette is normally filled with water.

Guzmania is native to tropical America. Leaves of the Guzmania are usually formed as basal rosettes which are stiff and entire and in several vertical ranks. Guzmania have terminal spikes or panicles which are often bracted with petals united in a tube about as long as the calyx.

Asexual propagation of Guzmania if frequently done through the use of tissue culture practices. Propagation can also be from off-shoots produced by the plant which may then be rooted. The resulting plantlets are detached from the mother plant and may be potted up in a suitable growing mixture.

The new cultivar Ultra is a product of a planned breeding program and was originated by the inventors from a cross made during such a program in Assendelft, The Netherlands, in 1985. The male, or pollen parent, was an unnamed selection from a mutation of *Guzmania lingulata lingulata*, identified by Code Number 84336128. The female, or seed parent, was an unnamed cultivar of *Guzmania lingulata minor*, identified by the Code Number 8433655. Both parents have a degree of homozygosity such that the progeny of the cross were and continue to be surprisingly uniform. The selection comprising the new variety was chosen after commencement of flowering of the progeny in 1987, and subsequent asexual propagation by offshoots has demonstrated that the combination of characteristics as herein disclosed for the new cultivar Ultra are firmly fixed and are retained through successive generations of asexual reproduction.

Ultra is particularly characterized by the following:

1. Strong, compact growth habit.
2. Dark purple inflorescence.
3. Superior floral bract production.
4. Star shaped inflorescence.
5. Relatively small in overall size and diameter when compared to other cultivars of this general type.

The closest comparison cultivar is Empire. Most of the characteristics described below for Ultra, except for the color of the inflorescence, are generally similar to those same characteristics of Empire. The floral bract color of the respective cultivars is very dissimilar. Whereas the bract color of Empire is a bright red, the bract color of Ultra is a deep purple, referred to in the color chart as a greyed-purple. Such color is very distinctive.

Ultra has not been tested under all available environmental conditions. The phenotype may slightly vary with variations in environmental conditions such as temperature, light intensity, day length and humidity, as well understood by those skilled in the art, without, however, any variance in genotype.

The accompanying color photographic drawings show typical characteristics of Ultra.

Sheet 1 comprises a top perspective view of a full plant with floral bracts, and wherein the bract color is accurately depicted.

The photograph at the top of sheet 2 is a side view showing foliage and inflorescence of a specimen plant, and the photograph at the bottom of sheet 2 is a more enlarged showing of the floral bracts and inflorescence.

The floral bract color shown in the photographs on Sheet 2 is not correct, with the true bract color being shown in the photographs comprising sheet 1, and above noted.

In the following description, color references are made to The Royal Horticultural Society Colour Chart (R.H.S.).

The following traits have been repeatedly observed and in combination distinguish Ultra as a new and distinct cultivar. These observations, measurements and descriptions have been performed under greenhouse conditions in Assendelft, The Netherlands.

I. Plant:

*Form.*—Funnel form rosette.

*Height.*—Short; approximately 20 cm high when flowering.

*Growth habit.*—Stemless.

*Diameter.*—Approximately 45 cm at time of flowering.

II. Foliage:

*Size of leaf.*—Approximately 27 to 30 cm long; leaves extend away from the base to form a full plant.

*Shape of leaf.*—Linear lanceolate.

*Surface texture.*—Smooth.

*Variegation.*—None.

*Color.*—Upperside; 146A; Underside; 146B; with greater amounts of fertilizer, the color can become slightly darker, in the range of 137A (upperside) and 137B (underside). During flowering, the center leaves can be infused in the middle with purple, approximately 186A.

III. Bracts:

*Length.*—Scape bracts: Approximately 8 to 14 cm. Primary bracts: Approximately 6 to 10 cm. Floral bracts: Approximately 5.5 cm.

*Width.*—Scape and primary bracts are approximately 2.5 cm, floral bracts approximately 1.4 cm.

*General shape.*—Ovate lanceolate.

*Texture.*—Smooth.

*Margin.*—Entire.

*Color.*—Upperside: When bud just opening 187A, becoming 187B during flowering; color of middle part of bracts toward center is 187C. Underside: 187D.

IV. Flowers:

*Borne.*—Erect on stalks, length of inflorescence being approximately 6 cm.

*Shape of inflorescence.*—Head.

*Individual petals.*—Length: Approximately 5 cm. Width: Approximately 0.5 cm. Quantity: Approximately 30 flowers, depending on the size of plant. Color of petals: R.H.S. 155D at top 0.3 cm; next approximately 1 cm is 8A, with color below that area becoming more translucent.

*Time of blooming.*—In a fully grown plant, flowers can bloom the whole year starting approximately 12 weeks after acetylene treatment.

*Duration of blooms.*—Each flower blooms 1 day and the total duration of blooming is about 6 weeks.

V. Reproductive organs:

*Ovaries.*—Superior.

*Stamens.*—6 in number.

VI. Seed characteristics:

*Quantity.*—Approximately 5000 seeds divided over approximately 20 capsules.

*Texture.*—The seeds are plumrose.

*Other.*—Not every plant has seed since not every plant makes seed. The seeds cannot be used for reproduction since characteristics cannot be passed through sexual propagation.

I claim:

1. A plant of a new and distinct cultivar of Guzmania plant named Ultra, as illustrated and described.

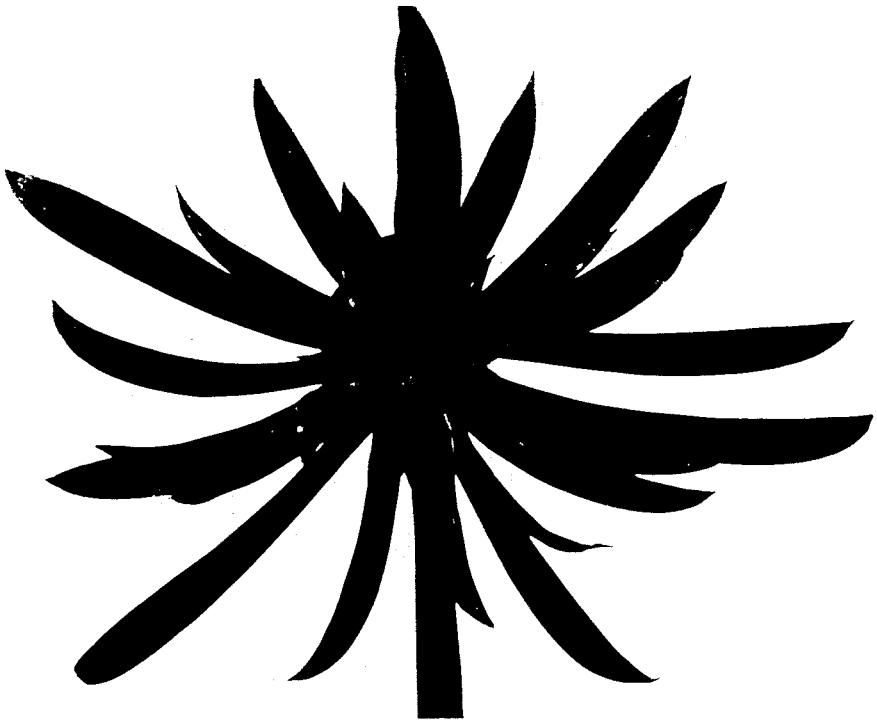

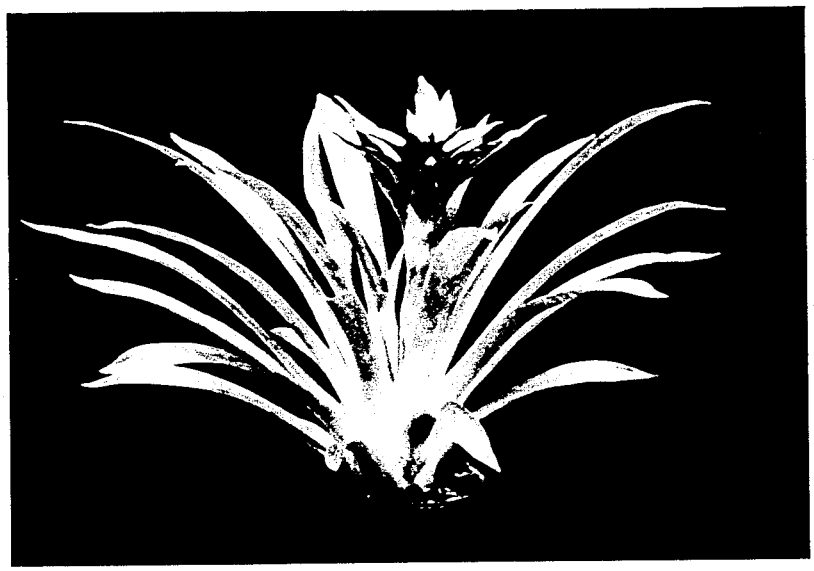
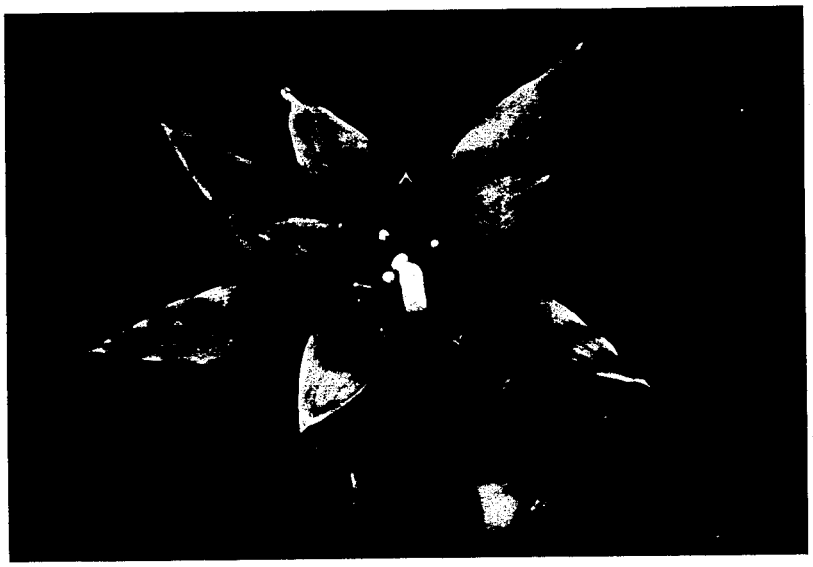

* * * * *